United States Patent [19]

Zardi et al.

[11] Patent Number: 5,130,098
[45] Date of Patent: Jul. 14, 1992

[54] SYSTEM TO IMPROVE THE EFFICIENCY OF HETEROGENEOUS REACTORS FOR EXOTHERMIC SYNTHESIS AND MORE PARTICULARLY FOR THE REACTION OF AMMONIA

[75] Inventors: Umberto Zardi, Via Lucino 57, CH-6900 Breganzona; Giorgio Pagani, Lugano, both of Switzerland

[73] Assignees: Ammonia Casale S. A.; Umberto Zardi, both of Switzerland

[21] Appl. No.: 587,527

[22] Filed: Sep. 24, 1990

Related U.S. Application Data

[63] Continuation of Ser. No. 159,399, Feb. 23, 1988, abandoned.

[30] Foreign Application Priority Data

Feb. 26, 1987 [CH] Switzerland .............. 00728/87

[51] Int. Cl.$^5$ ............................................. B01J 8/02
[52] U.S. Cl. ................................. 422/148; 422/194; 422/311; 423/361
[58] Field of Search .............. 422/148, 194, 311; 423/361

[56] References Cited

U.S. PATENT DOCUMENTS

| | | | |
|---|---|---|---|
| 4,244,922 | 1/1981 | Burke et al. | 422/311 X |
| 4,372,920 | 2/1983 | Zardi | 422/148 |
| 4,405,562 | 9/1983 | Zardi et al. | 422/148 |
| 4,632,587 | 12/1986 | Vollhardt | 422/202 |
| 4,755,362 | 7/1988 | Zardi | 422/148 |

Primary Examiner—Jill Johnston
Attorney, Agent, or Firm—Ostrolenk, Faber, Gerb & Soffen

[57] ABSTRACT

A system for modernizing exothermic heterogeneous reactors used in the synthesis of ammonia, methanol and the like, which include a pressure shell, a wall for forming an airspace, a wall or cartridge for containing a catalyst bed, and catalyst-containing basket. An airspace-forming wall is formed of a single piece substantially the whole axial length of the reactor. A bed forming wall is distinct from, and unconnected to, the airspace forming wall, and it constitutes independent modules, each module containing at least one catalyst bed and each module resting either on an underlying module or on an extension of an inside gas distribution collector. The bed forming walls contain the catalyst and distribute gas therethrough. A portion of the catalyst contacts the airspace-forming wall.

9 Claims, 4 Drawing Sheets

SYSTEM TO IMPROVE THE EFFICIENCY OF HETEROGENEOUS REACTORS FOR EXOTHERMIC SYNTHESIS AND MORE PARTICULARLY FOR THE REACTION OF AMMONIA

This is a continuation of application Ser. No. 07/159,399, filed on Feb. 23, 1988 and now abandoned.

BACKGROUND OF THE INVENTION

1. Field of the Invention

This invention concerns a system to modernize and improve the efficiency of reactors for exothermic heterogeneous synthesis, and more particularly for the synthesis of ammonia, methanol and the like, consisting in general of an external pressure shell, of a wall forming an airspace with the shell, of a wall delimiting the catalytic beds, of catalyst baskets, of tubes for the flow of synthesis gas and of tubes for the flow of quench gas.

2. Description of the Related Art

Reactors for heterogeneous synthesis and more particularly for the synthesis of ammonia consist generally of a pressure shell, of a wall forming an airspace, and of a cartridge with catalytic beds.

In some cases (see Kellogg axial flow and low height-/diameter H/D ratio reactors), the wall which with its external side forms the airspace with the shell, acts also with its internal face as wall delimiting the beds.

In other cases (Topsoe, for example) the wall forming an airspace is separate and distinct from the wall of the cartridge forming beds, cartridge which is this case is generally in a single piece, and monolithic, that is to say inseparable for the single beds.

In a more recent instance (Ammonia Casale system) the external wall forming the airspace is inseparable from the wall of the cartridge forming the beds and is formed by separable modular parts, each containing at least one catalyst bed.

Continuing now their research, the Applicants have surprisingly noted that the operating efficiency of these as well as of other reactors can be remarkably improved by making easily and economically achieved structural changes.

SUMMARY OF THE INVENTION

It has been found, in effect, that the optimal solution for modernizing practically all current reactor exception made for conventional "bottle-neck" Kellogg reactors consists in providing:

a) a one-piece wall forming an airspace (with the shell);
b) a wall formings beds which is totally separate and has no connection with the wall forming the airspace but consists instead of detached modules, each of them delimiting at least one catalytic bed, each module resting on the underlying module, and being formed by the wall delimiting the catalyst and the wall distributing the gas;
c) the contact of portions of catalyst with sections of the wall forming the airspace, and
d) at least a part of the independent modules, each delimiting at least one catalytic bed, rests preferably on the underlying module by means of extending the internal gas distribution collector.

In a preferred embodiment of the invention, the top catalytic beds have part of the catalyst in contact with minor portion of the airspace a) said part being run through axially by the synthesis gas, the major portion of catalyst detached from the airspace is run through by synthesis gas with an outward radial flow, and at least the bottom bed has a minor portion of catalyst no longer in contact with wall a) but with a section of unperforated central wall, which could be for example a section of the central gas tube, the major portion of catalyst detached from said section of wall being run through with an inward radial flow.

BRIEF DESCRIPTION OF THE DRAWINGS

Other features and advantages of the present invention will become apparent when the following description is read in conjunction with the accompanying drawings in which.

DETAILED DESCRIPTION OF THE PREFERRED EMBODIMENTS

According to a particularly advantageous feature of the invention, the quench gas flows into the above-mentioned airspace areas next o the lower ends of the catalytic areas in contact with the wall forming the airspace a).

The various aspects and advantages of the invention will be better illustrated by the following description of a preferred reactor embodiment (achieved for example by modernizing a particular type of reactor).

Figure 1:
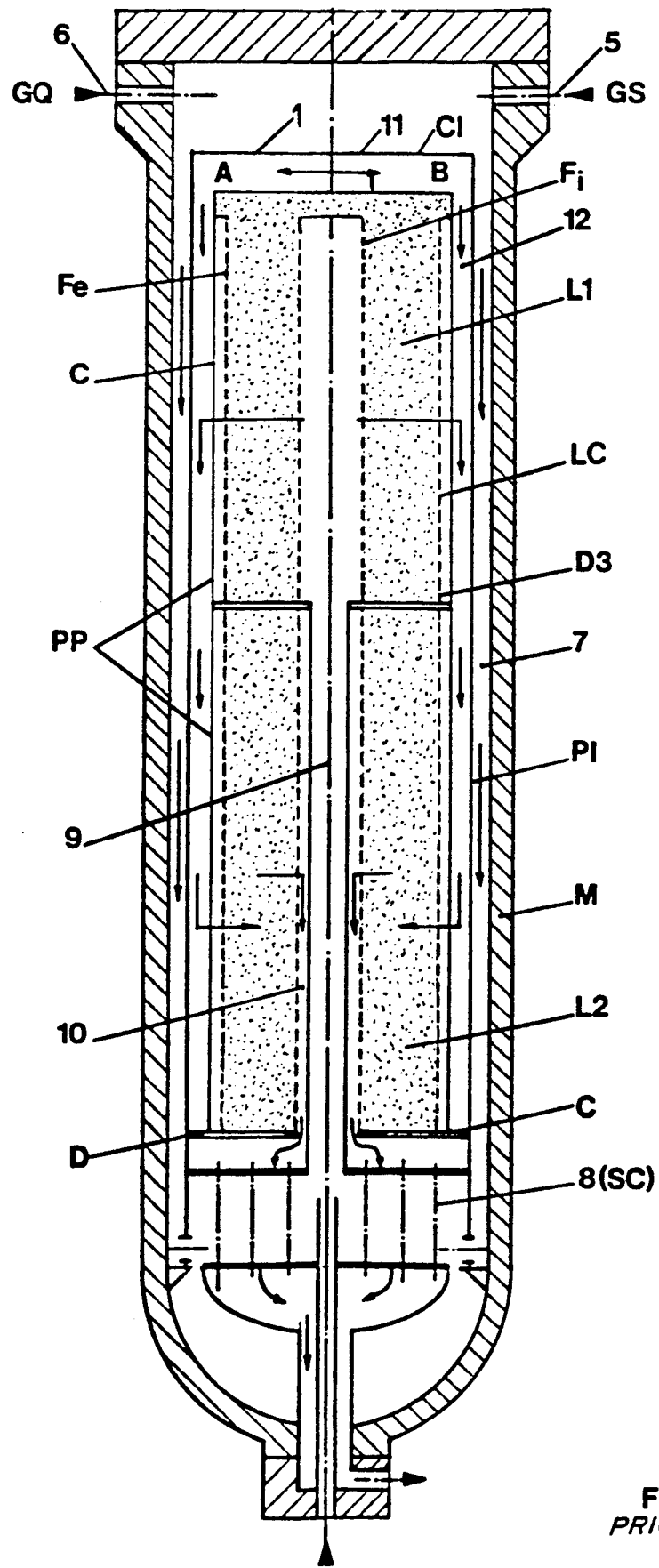
FIG. 1 shows a longitudinal cross-sectional view of a known synthesis gas reactor.

In order to define matters straight away and refer to one of the many conventional reactors capable of modernization, FIG. 1 shows in longitudinal cross-section a typical Topsoe (Series 100) reactor consisting of an outer shell M, of an inner closed shell I with airspace forming wall PI and cover CI, and of the cartridge with catalytic beds C which has, going from the outside to the inside, a solid wall PP and two perforated walls or concentric nets Fe and Fi delimiting the catalytic bed LC which is divided into an upper bed L1 and a lower bed L2, and of a baffle plate separating the beds D3. The synthesis gas GS enters via duct 5, flows along airspace 7, goes into heat exchanger 8, flows upwards along central tube 9 and then runs radially through beds L1 and L2 collecting in annular inner space 10, and feeding, before leaving the reactor, exchanger 8 inside the tubes. From duct 6 quench gas GQ enters, flowing directly from the lid 11 of inner shell I, and mixes with the reacted synthesis gas coming from bed 1.

Conversion yields of these reactors are relatively low, with the disadvantage that their energy consumption is rather high.

The aim of this invention is a system to modernize in situ any type of conventional reactor (excluding reactors with "bottle-neck" shells) transforming it very easily and simply into an axial-radial reactor preferably with the quenching taking place at the end of the axial flow zone.

Another aim of the invention is to modify in situ the structure of these reactors and to increase substantially yields while at the same time reducing energy consumption.

A conventional reactor as shown in FIG. 1 can be modernized by removing the inner shell for example ABDC, while leaving unchanged the outer shell and possibly the wall forming an airspace with said shell.

Figure 2:
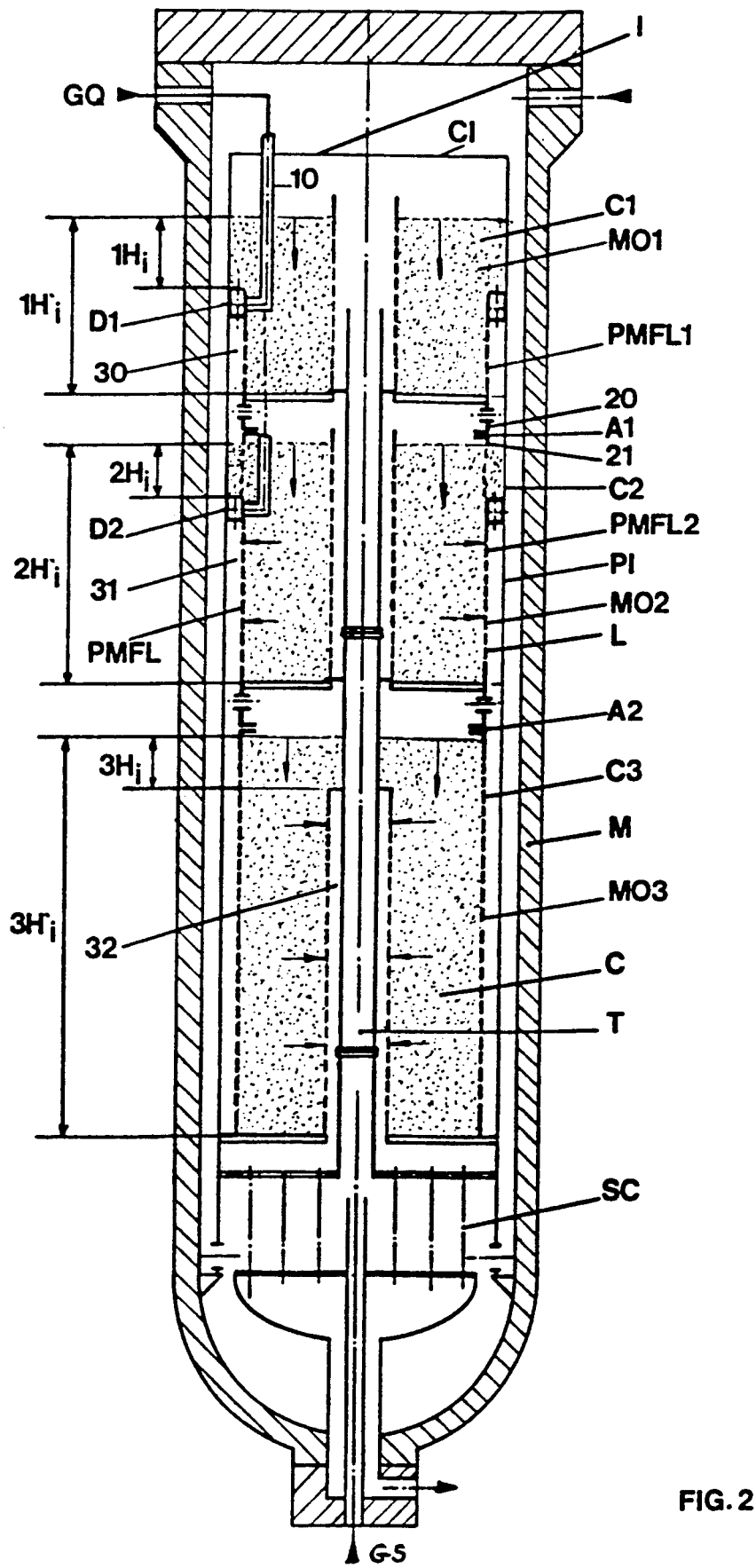
FIG. 2 shows a reactor in accordance with the invention.

FIG. 2 shows the optimal reactor achieved by using the system according to the invention, in which the outer shell M and the inner closed shell I, with airspace forming wall in a single piece PI and cover CI, are maintained. According to an aspect of the invention the wall forming catalytic beds C1, C2 ... Cn (in the case represented by n=3), PMFL is formed by modules characterised by the fact that each module is formed by wall L which beside delimiting catalyst C and distributing through it synthesis gas GS, now also acts as support for the upper module. As FIG. 2 shows, the wall PMFL1 of upper module MO1 has an appendix or extension 20 which finds support in A1, that is to say on an extension 21 of wall PMFL2 of module MO2. The same applies for supporting in A2 module MO2, resting on module MO3.

According to a further remarkable aspect of the invention, portions of height 1Hi, 2Hi, etc. of catalyst C1 and respectively C2 in modules MO1 respectively MO2, are in contact with the airspace forming wall PI. On these portions of catalyst of height 1Hi, 2Hi, etc. the synthesis gas (which enters from the bottom, runs through heat exchanger SC and flows downwards again into the catalytic beds) flows axially whereas in the major portions of catalyst 1H'i-1Hi, 2H'i-2Hi the gas flows radially outwards collecting in the annular areas from 30 where it flows over catalyst C2 of the following module MO2, through which it will flow again axially on the portion of height 2Hi and will flow radially outwards through major portion 2H'i-2Hi.

Preferably and in accordance with the specification of a very recent Swiss patent application by the Applicants, in areas 30 and 31 quench gas GQ flows in through duct 10 and annular distributor D1, respectively D2, which are placed directly at the end of the catalytic portion of height 1Hi, and 2Hi respectively.

The description of that patent application which is Swiss Patent Application 00494/87-6, filed Feb. 11, 1987 is deemed to be incorporated herein to better illustrate the aspects and advantages of this quench system.

In FIG. 2 two beds have been shown, C1 and C2, in modules MO1 and MO2 "OUTWARDS" with portions of catalyst of height 1Hi, respectively 2Hi, in contact with airspace forming wall PI. Obviously the number of outwards modules may be other than 2, better still if greater than 2. Still in FIG. 2, the third catalytic bed C3 in module MO3 is run through by gas inwardly and the top part of the bed of height 3Hi run through axially by the gas is delimited inside by a portion of the central gas tube t, while the major portion of catalyst C3 of height 3H'i-3Hi is run through inwards radially collecting in annular areas 32. Preferably the height of catalytic beds 1H'i, 2H'i, 3H'i, etc., increases on the way towards the lower baskets. The "inwards" module MO3 does not receive any quench gas. For greater details concerning these aspects reference is made also to published European patent application 202454 and U.S. Pat. Nos. 4,372,920 and 4,405,562 in the Applicants' name.

Figure 3:
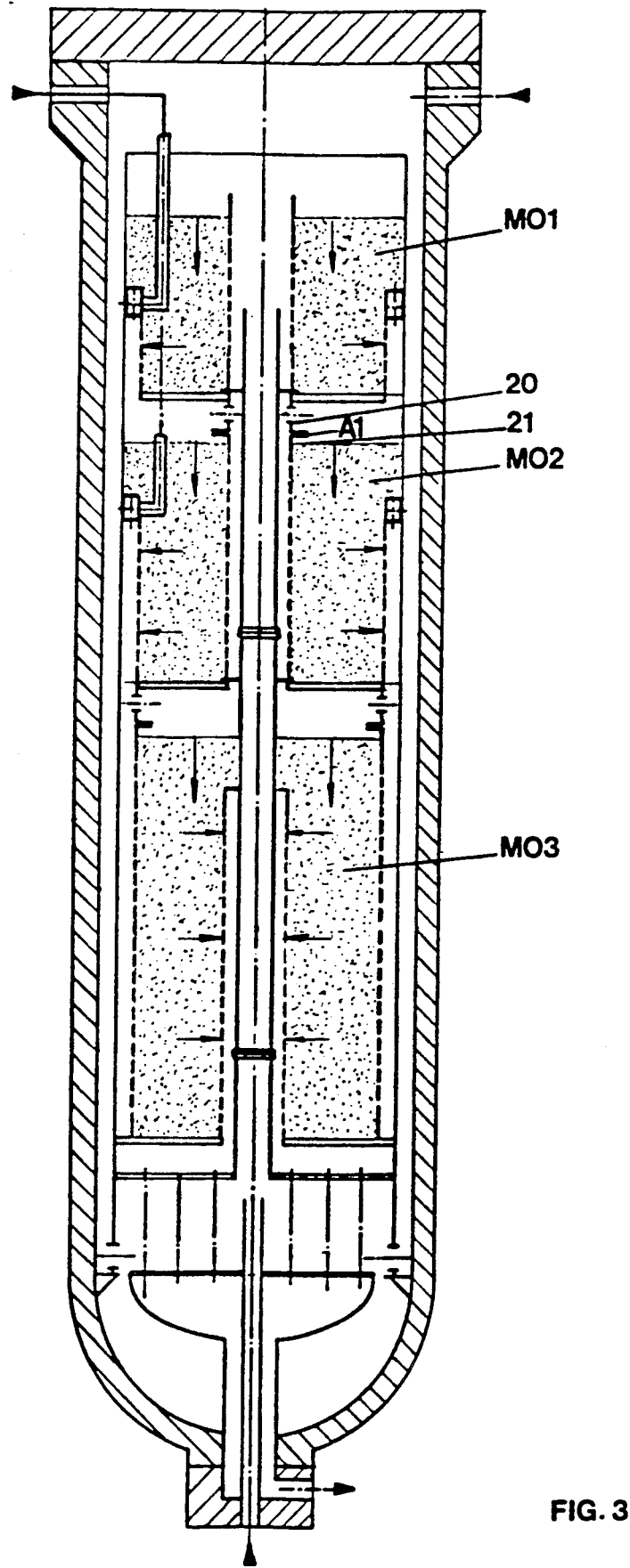
FIG. 3 shows a preferred embodiment of the invention wherein a first catalyst module rests on an underlying module by means of an extension of the internal gas collector.

According to a preferred embodiment of the invention shown in FIG. 3, the first module MO1 rests on the underlying module by means of extension 20 of the internal gas collector, which rests in A1 on the extension 21 of the internal gas collector of the underlying module MO2.

Figure 4:
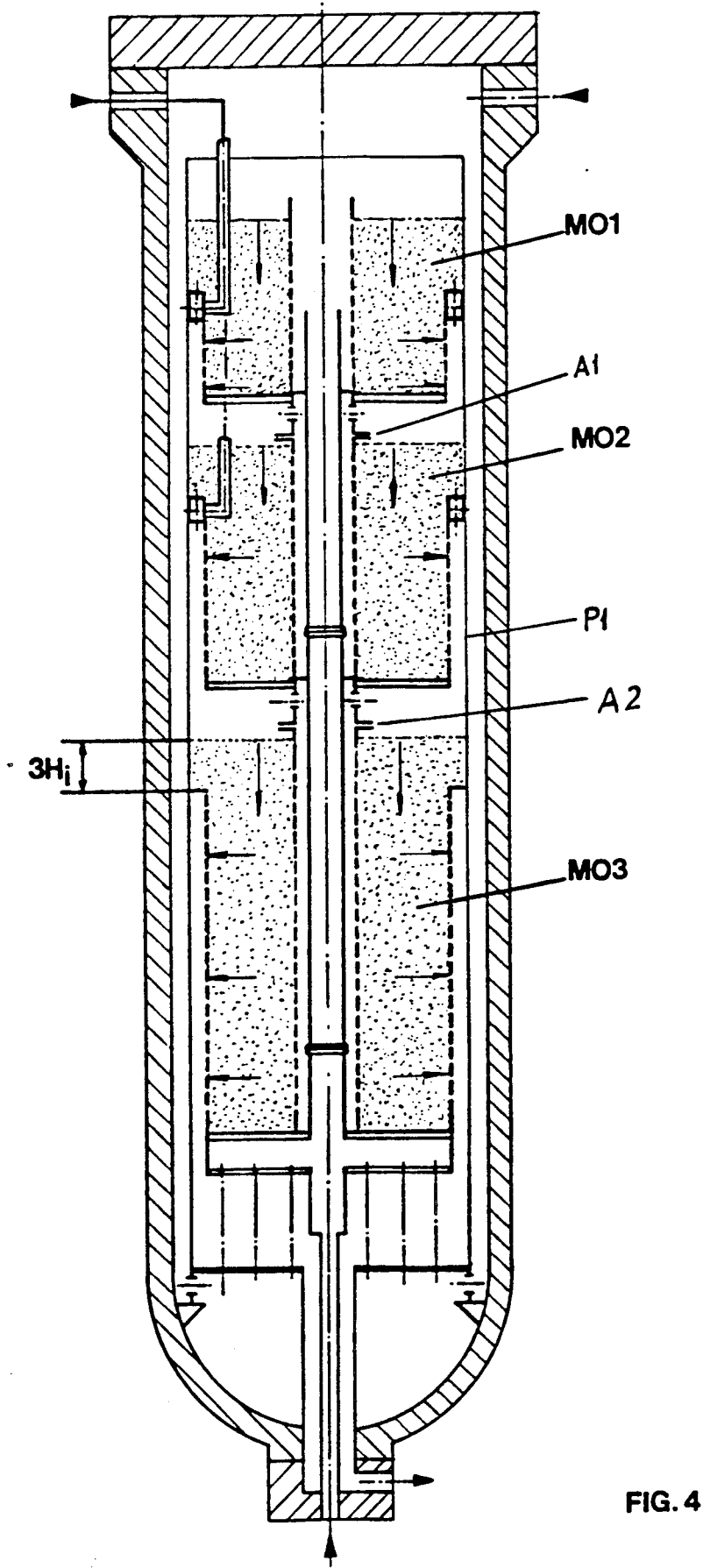
FIG. 4 shows a further embodiment of the invention wherein both a first and second module rest on an underlying module by means of an extension of the internal gas collector.

According to a further embodiment of the invention shown in FIG. 4, both modules MO1 and MO2 rest on the underlying module on support A1 (respectively A2) formed by the extension of the internal gas collectors. Furthermore, all three beds are "outwards" and also portion 3Hi of the third bed, run through by the gas axially, is delimited by a portion of the airspace forming wall PI.

We claim:

1. A system for modernizing and improving the efficiency of a reactor for exothermic heterogeneous synthesis, the reactor comprising an external pressure shell, a wall forming an airspace wit the shell, a plurality of catalytic beds, a plurality of catalyst baskets, a plurality of feed ducts for synthesis gas and a plurality of feed ducts for quench gas, wherein the improvement comprises:

a) said airspace forming wall in a single piece; and
 b) said catalyst baskets are entirely distinct and totally unconnected to said airspace-forming wall and consist of detached modules, each module delimiting at least one catalytic bed, each module being stacked on top of and fully supported by an underlying module, a lowermost module being supported by said airspace-forming wall, each module being formed by gas permeable walls which contain catalyst and distribute therethrough said synthesis gas and each module having at least one extension associated therewith for resting said modules on top of each other;
 c) wherein said airspace-forming wall has portions in contact with said catalyst in a plurality of beds.

2. The system according to claim 1, wherein at least one catalytic bed has a section of catalyst contained therein in contact with minor portions of said airspace-forming wall, said catalyst section contacting said airspace-forming wall being run through axially by said synthesis gas, the remaining catalyst in said one catalyst bed being run through by said synthesis gas with an outward radial flow.

3. The system according to claim 2, further comprising a wall centrally disposed within the reactor, at least one catalyst bed having a minor portion of catalyst in contact with an unperforated section of said central wall, and the major portion of catalyst not in contact with said central wall being run through with an inward radial flow.

4. The system according to claim 3, wherein said central wall forms a central gas tube.

5. The system according to claim 2, wherein said feed ducts for quench gas introduce quench gas at a bottom of said section of catalyst bed in contact with said airspace-forming wall.

6. The system according to claim 3, wherein said at least one extension is an extension of said central wall.

7. A reactor for heterogeneous synthesis, comprising a shell; an airspace-forming wall which is closed in an upper part and which is a single piece substantially for an entire axial length of said reactor; and a plurality of stacked, modular catalyst baskets for containing a plurality of catalytic beds, said catalyst baskets being entirely distinct and detached from said airspace-forming wall each catalyst basket having at least one extension associated therewith for resting said catalyst baskets on top of each other; wherein a portion of catalyst contained in at least one catalyst bed is in contact with said airspace-forming wall and at least another portion of said catalyst contained therein is spaced from said airspace-forming wall.

8. The reactor of claim 7, further comprising an unperforated wall centrally located within said reactor.

9. The reactor of claim 8, wherein a portion of catalyst contained in at least one catalytic bed is in contact with section of said unperforated central wall.

* * * * *